(12) United States Patent
Tekumalla et al.

(10) Patent No.: US 10,460,074 B2
(45) Date of Patent: *Oct. 29, 2019

(54) METHODS AND SYSTEMS FOR PREDICTING A HEALTH CONDITION OF A HUMAN SUBJECT

(71) Applicant: Conduent Business Services, LLC, Dallas, TX (US)

(72) Inventors: Lavanya Sita Tekumalla, Bangalore (IN); Vaibhav Rajan, Bangalore (IN)

(73) Assignee: CONDUENT BUSINESS SERVICES, LLC, Florham Park, NJ (US)

( * ) Notice: Subject to any disclaimer, the term of this patent is extended or adjusted under 35 U.S.C. 154(b) by 260 days.

This patent is subject to a terminal disclaimer.

(21) Appl. No.: 15/090,710

(22) Filed: Apr. 5, 2016

(65) Prior Publication Data
US 2017/0286623 A1 Oct. 5, 2017

(51) Int. Cl.
*G16H 50/30* (2018.01)
*G06F 19/00* (2018.01)

(52) U.S. Cl.
CPC ............. *G06F 19/00* (2013.01); *G16H 50/30* (2018.01)

(58) Field of Classification Search
CPC .... G06F 19/3431; G06F 19/00; G06F 16/285; G16H 50/30; A61B 5/7267; G09B 23/281; G09B 23/32; G09B 23/34; G09B 17/00; G09B 17/003; G09B 17/04; G09B 19/04; G09B 19/06; G09B 7/02
See application file for complete search history.

(56) References Cited

U.S. PATENT DOCUMENTS

| 4,783,803 A | * | 11/1988 | Baker | ..................... G10L 15/00 704/252 |
| 2001/0051765 A1 | * | 12/2001 | Walker | .................. A61B 5/1112 600/300 |
| 2005/0059017 A1 | * | 3/2005 | Oldham | .................... G01J 1/42 435/6.13 |

(Continued)

OTHER PUBLICATIONS

C. Genest, K. Ghoudi, and L.-P. Rivest. A semiparametric estimation procedure of dependence parameters in multivariate families of distributions. Biometrika, 82(3):543{552, 1995.

(Continued)

*Primary Examiner* — Neal Sereboff
(74) *Attorney, Agent, or Firm* — Jones Robb, PLLC

(57) ABSTRACT

Disclosed are embodiments of methods and systems for predicting a health condition of a first human subject. The method comprises receiving a measure of one or more physiological parameters associated with the first human subject. The method estimates one or more latent variables based on a first count indicative of a number of the plurality of d-vines, a second count indicative of a number of the one or more records, a first value that is representative of a number of the one or more records clustered into a d-vine from the plurality of d-vines, and a second value that is representative of a parameter utilizable to predict a third value. The method generates the plurality of d-vines based on the estimated one or more latent variables. The method predicts health condition of the first human subject by utilizing a trained classifier based on the estimated one or more latent variables.

17 Claims, 3 Drawing Sheets

(56) References Cited

U.S. PATENT DOCUMENTS

| | | | | |
|---|---|---|---|---|
| 2005/0278140 | A1* | 12/2005 | Wang | G01R 31/2894 702/179 |
| 2011/0119212 | A1* | 5/2011 | De Bruin | A61B 5/00 706/12 |
| 2012/0095300 | A1* | 4/2012 | McNair | A61B 5/021 600/300 |
| 2012/0143017 | A1* | 6/2012 | Snyder | G06N 20/00 600/300 |
| 2012/0203166 | A1* | 8/2012 | Riback | A61B 5/14532 604/66 |
| 2012/0223889 | A1* | 9/2012 | Medlock | G06F 3/04883 345/168 |
| 2012/0288881 | A1* | 11/2012 | Liu | G01N 33/6893 435/7.92 |
| 2012/0290599 | A1* | 11/2012 | Tian | G06F 16/313 707/758 |
| 2015/0227691 | A1* | 8/2015 | Bhattacharya | G06N 7/005 705/3 |

OTHER PUBLICATIONS

Claudia Czado Aleksey Min. Bayesian inference for multivariate copulas using pair-copula constructions. Journal of Financial Econo-Metrics, pp. 511{546, 2010.

Marina Meila. Comparing clusterings: an information based distance. Journal of Multivariate Analysis, 98(5):873{895, 2007.

Paul Embrechts, Alexander McNeil, and Daniel Straumann. Correlation and dependence in risk management: properties and pitfalls. Risk management: value at risk and beyond, pp. 176{223, 2002.

Peter Ho. Extending the rank likelihood for semiparametric copula estimation. The Annals of Applied Statistics, 1(1):265{283, 2007.

Harry Joe. Families of m-variate distributions with given margins and m (m-1)/2 bivariate dependence parameters. Lecture Notes—Monograph Series, pp. 120{141, 1996.

SM Liao YS Jung D Kim, JM Kim. Mixture of d-vine copulas for modeling dependence. Computational Statistics and Data Analysis, pp. 64, 1 { 9, 2013.

Ingmar Nolte. Modeling a multivariate transaction process. Journal of Financial Econometrics, 6(1):143{170, 2008.

Paul Embrechts, Filip Lindskog, and Alexander McNeil. Modelling dependence with copulas and applications to risk management. Handbook of heavy tailed distributions in finance, 8(1):329{384, 2003.

Andrew J Patton. On the out-of-sample importance of skewness and asymmetric dependence for asset allocation. Journal of Financial Econometrics, 2(1):130{168, 2004.

Kjersti Aas, Claudia Czado, Arnoldo Frigessi, and Henrik Bakken. Pair-copula constructions of multiple dependence. Insurance: Mathematics and economics, 44(2):182{198, 2009.

Zoubin Ghahramani. Unsupervised learning. In Advanced Lectures on Machine Learning, pp. 72{112. Springer-Verlag, 2004.

Michael S.Smith and Mohamad A. Khaled. Estimation of copula models with discrete margins via bayesian data augmentation. Journal of the American Statistical Association, Theory and Methods Section, 2011.

* cited by examiner

METHODS AND SYSTEMS FOR PREDICTING A HEALTH CONDITION OF A HUMAN SUBJECT

TECHNICAL FIELD

The presently disclosed embodiments are related, in general, to healthcare. More particularly, the presently disclosed embodiments are related to methods and systems for predicting a health condition of a human subject.

BACKGROUND

The healthcare industry, among various modern day industries, may produce data at a staggering rate. Managing this data and drawing meaningful conclusions and insights may be critical for the operational success of organizations of this industry. For instance, the healthcare industry may maintain various types of records of human subjects/patients such as, but not limited to, medical diagnosis records, medical insurance records, hospital data, etc. The records of the human subjects/patients may be analyzed using various mathematical models to identify trends and categorize the data into different risk profiles (e.g., risk of contacting a disease, life expectancy, and health insurance risk profile).

Typically, the data, which is to be analyzed, may include fields of various types. For example, medical records may include various fields of numerical data type, for instance, BP measure, heart rate, and blood sugar measure. Further, the medical records may also include various fields of categorical data type, for example, gender. Categorization of records of such varied types may be cumbersome as a mathematical model suited to categorize data of one type may not work well with data of another type. Thus, categorization of mixed data (i.e., numerical and categorical) may be difficult. Further, analysis of records of a large number of fields exacerbates the already difficult task.

SUMMARY

According to embodiments illustrated herein there is provided a method to predict a health condition of a first human subject. The method may receive a measure of one or more physiological parameters associated with the first human subject. The one or more physiological parameters include at least one of an age, a cholesterol level, a heart rate, a blood pressure, a breath carbon-dioxide concentration, a breath oxygen concentration, a stroke score, a blood creatinine level, a blood albumin level, a blood sodium level, a total blood count, a blood glucose/sugar level, a blood hemoglobin level, and a blood platelet count. The method may further extract a historical data. The historical data includes a measure of the one or more physiological parameters associated with each of one or more second human subjects. The method may further cluster the historical data into a plurality of d-vines by sampling a plurality of latent variables based on a rank transformation of the historical data. The method may further estimate one or more latent variables from the plurality of latent variables based on a first count indicative of a number of the plurality of d-vines, a second count indicative of a number of the one or more records, a first value that is representative of a number of the one or more records, and a second value that is representative of a parameter utilizable to predict a third value. The third value corresponds to a probability of clustering the historical data into the d-vine from the plurality of d-vines. The method may further generate the plurality of d-vines based on the estimated one or more latent variables from the plurality of latent variables. The method may further train a classifier based on the generated plurality of d-vines. The method may further predict the health condition of the first human subject by utilizing the classifier based on the received measure of the one or more physiological parameters associated with the first human subject.

According to embodiment illustrated herein there is provided a system that comprises an application server configured to predict a health condition of a first human subject. The application server may comprise one or more processors configured to receive a measure of one or more physiological parameters associated with the first human subject. The one or more physiological parameters include at least one of an age, a cholesterol level, a heart rate, a blood pressure, a breath carbon-dioxide concentration, a breath oxygen concentration, a stroke score, a blood creatinine level, a blood albumin level, a blood sodium level, a total blood count, a blood glucose/sugar level, a blood hemoglobin level, and a blood platelet count. The one or more processors may further be configured to extract a historical data comprising a measure of the one or more physiological parameters associated with each of one or more second human subjects. The one or more processors may further be configured to cluster the historical data into a plurality of d-vines by sampling a plurality of latent variables based on a rank transformation of the historical data. The one or more processors may further be configured to estimate one or more latent variables from the plurality of latent variables based on a first count indicative of a number of the plurality of d-vines, a second count indicative of a number of the one or more records, a first value that is representative of a number of the one or more records clustered into a d-vine from the plurality of d-vines, and a second value that is representative of a parameter utilizable to predict a third value. The third value corresponds to a probability of clustering the historical data into the d-vine from the plurality of d-vines. The one or more processors may further be configured to generate the plurality of d-vines based on the estimated one or more latent variables from the plurality of latent variables. The one or more processors may further be configured to train a classifier based on the generated plurality of d-vines. The one or more processors may further be configured to predict the health condition of the first human subject by utilizing the classifier based on the received measure of the one or more physiological parameters associated with the first human subject.

According to embodiments illustrated herein, there is provided a computer program product for use with a computing device. The computer program product comprises a non-transitory computer readable medium storing a computer program code for predicting a health condition of a first human subject. The computer program code is executable by one or more processors in the computing device to receive a measure of one or more physiological parameters associated with a first human subject. The one or more physiological parameters comprise at least one of an age, a cholesterol level, a heart rate, a blood pressure, a breath carbon-dioxide concentration, a breath oxygen concentration, a stroke score, a blood creatinine level, a blood albumin level, a blood sodium level, a total blood count, a blood glucose/sugar level, a blood hemoglobin level, and a blood platelet count. The computer program code is further executable by the one or more processors to extract a historical data comprising one or more records, wherein each of the one or more records includes a measure of the one or more physiological parameters associated with each of one or more second human subjects. The computer program code is further executable by the one or more processors to cluster the historical data into a plurality of d-vines by sampling a plurality of latent variables based on a rank transformation of the historical data. The computer program code is further executable by the one or more processors to estimate one or more latent variables from the plurality of latent variables based on: a first count indicative of a number of the plurality of d-vines, a second count indicative of a number of the one or more records, a first value that is representative of a number of the one or more records clustered into a d-vine from the plurality of d-vines, and a second value that is representative of a parameter utilizable to predict a third value, wherein the third value corresponds to a probability of clustering the historical data into the d-vine from the plurality of d-vines. The computer program code is further executable by the one or more processors to generate the plurality of d-vines based on the estimated one or more latent variables from the plurality of latent variables. The computer program code is further executable by the one or more processors to train a classifier based on the generated plurality of d-vines. The computer program code is further executable by the one or more processors to predict a health condition of the first human subject by utilizing the classifier based on the received measure of the one or more physiological parameters associated with the first human subject.

BRIEF DESCRIPTION OF DRAWINGS

The accompanying drawings illustrate various embodiments of systems, methods, and other aspects of the disclosure. Any person having ordinary skill in the art will appreciate that the illustrated element boundaries (e.g., boxes, groups of boxes, or other shapes) in the figures represent one example of the boundaries. It may be that in some examples, one element may be designed as multiple elements or that multiple elements may be designed as one element. In some examples, an element shown as an internal component of one element may be implemented as an external component in another, and vice versa. Furthermore, elements may not be drawn to scale.

Various embodiments will hereinafter be described in accordance with the appended drawings, which are provided to illustrate, and not limit, the scope in any manner, wherein similar designations denote similar elements, and in which.

DETAILED DESCRIPTION

Figure 1:
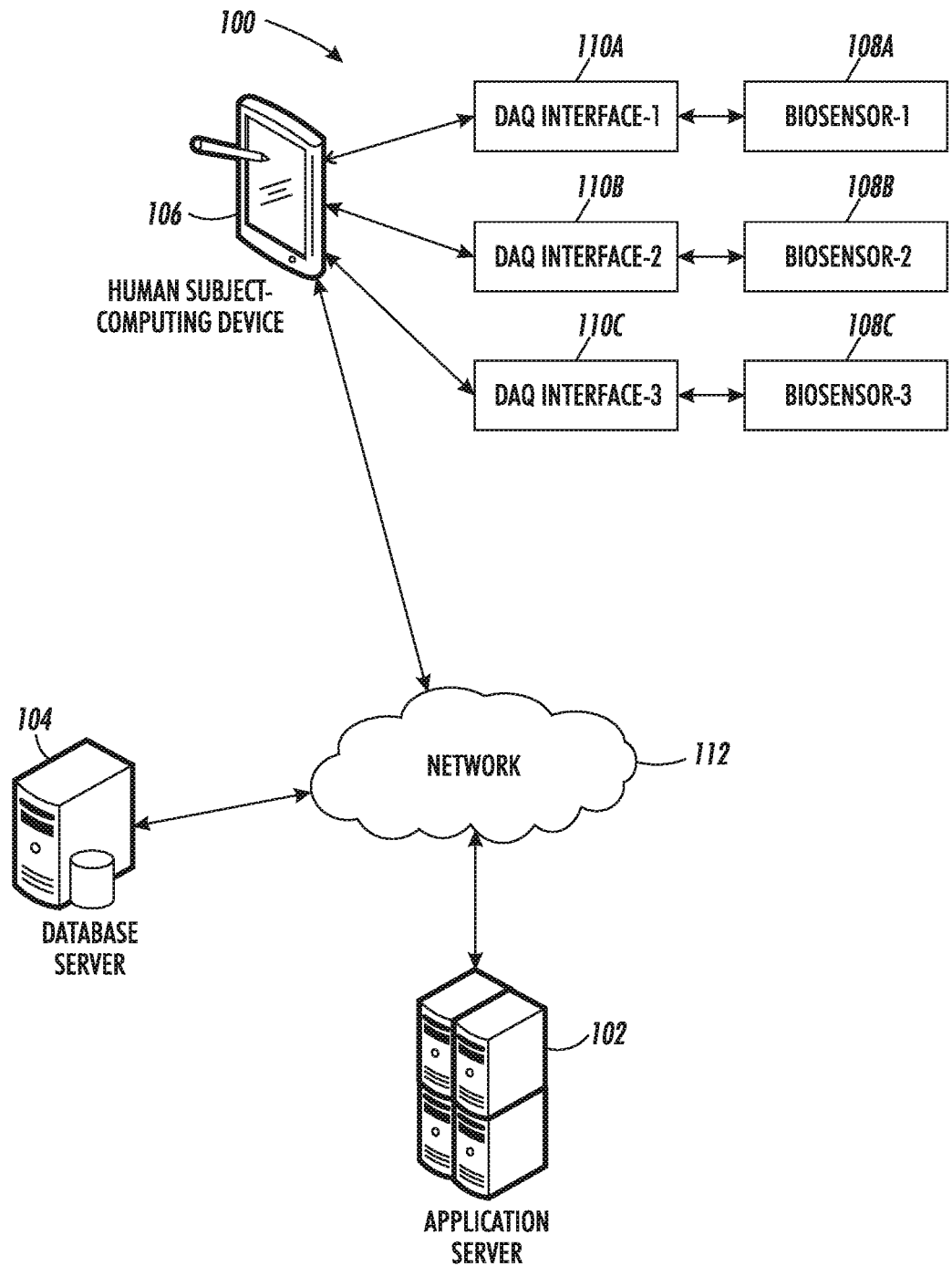
FIG. 1 is a block diagram of a system environment, in which various embodiments can be implemented.

The present disclosure is best understood with reference to the detailed figures and descriptions set forth herein. Various embodiments are discussed below with reference to the figures. However, those skilled in the art will readily appreciate that the detailed descriptions given herein with respect to the figures are simply for explanatory purposes, as the methods and systems may extend beyond the described embodiments. For example, the teachings presented and the needs of a particular application may yield multiple alternate and suitable approaches to implement the functionality of any detail described herein. Therefore, any approach may extend beyond the particular implementation choices in the following embodiments described and shown.

References to "one embodiment," "at least one embodiment," "an embodiment," "one example", "an example", "for example" and so on, indicate that the embodiment(s) or example(s) so described may include a particular feature, structure, characteristic, property, element, or limitation, but that not every embodiment or example necessarily includes that particular feature, structure, characteristic, property, element, or limitation. Furthermore, repeated use of the phrase "in an embodiment" does not necessarily refer to the same embodiment.

Definitions: The following terms shall have, for the purposes of this application, the respective meanings set forth below.

A "multivariate dataset" refers to a dataset that includes observations of an m-dimensional variable. For example, "n" observations of m-dimensional variable may constitute a multivariate dataset. For example, a medical record data may include a measure of one or more physiological parameters of one or more patients, where the one or more physiological parameters correspond to the m-dimensions and the one or more patients correspond to n observations. Such medical record data is an example of the multivariate dataset.

"Historical data" refers to a dataset that may be generated over a period. The historical data may include records associated with one or more subjects or events. Each record may include one or more fields, each of which may correspond to an individual observation related to a measured parameter.

A "healthcare dataset" refers to a multivariate dataset that includes data obtained from the healthcare industry. In an embodiment, the healthcare dataset may correspond to a patient record data, hospital data, medical insurance data, diagnostics data, etc. In a scenario, where the healthcare data corresponds to the patient record data, the one or more physiological parameters correspond to the m-dimensional variable, and the number of records in the healthcare data corresponds to the observations.

A "human subject" corresponds to a human being, who may have a health condition or a disease. In an embodiment, the human subject may correspond to a person who seeks a medical opinion on his/her health condition.

A "Data-Acquisition (DAQ) device" refers to a device, which may gather signals from an external stimulus and generate output usable by a computing device for further processing. For example, a DAQ device may correspond to a temperature sensor that measures a surface temperature of a substrate and generates a corresponding temperature reading for further processing by a computing device.

A "DAQ interface" refers to an interface that facilitates communication between a DAQ device and a computing device. In an embodiment, to facilitate communication between a DAQ device and a computing device connected through the DAQ interface, the DAQ interface may convert a signal of a first format, generated by the DAQ device, to a signal of a second format, acceptable by the computing device, and vice versa. For instance, the DAQ interface may convert analogue signals generated by a DAQ device to corresponding digital signals, acceptable by a computing device. Further, the DAQ interface may serialize or parallelize the digital signals in accordance with data-input requirements of the computing device. Examples of the DAQ interface include, but are not limited to, a Universal Serial Bus (USB) Port, a FireWire Port, an IEEE 1394 standard based connector, or any other serial/parallel data interfacing connector known in the art.

"Biosensor" refers to a DAQ device that can be used to measure one or more physiological parameters of a human subject. Examples of a biosensor include, but are not limited to, a pressure/pulse sensor (to measure a blood pressure and heart rate), a temperature sensor (to measure a body temperature), a blood sample analyzer (to measure readings of various blood-tests such as a blood creatinine level, a blood albumin level, a blood sodium level, a total blood count, a blood glucose/sugar level, a blood hemoglobin level, and a blood platelet count, a cholesterol level), a breath analyzer (to measure a breath carbon-dioxide/oxygen concentration), and so on.

A "copula" refers to a multivariate probability distribution of a multivariate dataset, which may be used to decouple dependencies among various dimensions of the multivariate dataset. In an embodiment, the copula may be represented as a function of constituent univariate marginal distributions of the various dimensions in the multivariate dataset. In an embodiment, the univariate marginal distributions may be uniformly distributed. In an embodiment, an m-dimensional copula may be represented as a multivariate distribution function C: $[0,1]^m \rightarrow [0,1]$. The following equation represents a relationship between a joint distribution function F and univariate marginal distributions $F_1(X_1)$, $F_2(X_2)$, ... $F_m(X_m)$ of an m-dimensional multivariate dataset using an m-dimensional Copula function C:

$$F(X_1, X_2, \ldots X_m) = C(F_1(X_1), F_2(X_2), \ldots F_m(X_m)) \quad (1)$$

where,

Xi: a random variable for the $i^{th}$ dimension of the m-dimensional multivariate dataset (e.g., a measure of a physiological parameter in a multivariate healthcare dataset);

$F_i(X_i)$: a univariate marginal distribution for the $i^{th}$ dimension of the m-dimensional multivariate dataset, where $U_i \leq F_i(X_i)$, $U_i$: a cumulative distribution of $X_i$;

F( ) a joint distribution function of the m-dimensional multivariate dataset; and C( ): an m-dimensional copula function.

A "joint density function" refers to a joint probability distribution of a multivariate dataset. In an embodiment, the joint density function may represent a probability of assigning values to various dimensions of the multivariate dataset within a respective range associated with each dimension. In an embodiment, a joint density function f of a m-dimensional multivariate dataset may be expressed in terms of an m-dimensional copula density function and univariate marginal density functions $f_1, f_2, \ldots f_m$ as follows:

$$f(X_1, X_2, \ldots X_m) = c_{1 \ldots m}(F_1(X_1), F_2(X_2), \ldots F_m(X_m)) \cdot f_1(X_1) \cdot f_2(X_2) \ldots f_m(X_m) \quad (2)$$

where, f( ) a joint density function of the m-dimensional multivariate dataset;

$f_i(X_i)$: a marginal density function of $X_i$; and $c_{1 \ldots m}$: an m-dimensional copula density function, where, $$c_{1 \ldots m}(F_1(X_1), F_2(X_2), \ldots F_m(X_m)) = \frac{\delta C}{\delta F_1 \delta F_2 \ldots \delta F_m} C(F_1(X_1), F_2(X_2), \ldots F_m(X_m)) \quad (3)$$

In an embodiment, the joint density function f of the m-dimensional multivariate dataset may also be expressed in terms of conditional densities of the random variables as follows:

$$f(X_1, X_2, \ldots X_m) = f_m(X_m) \cdot f(X_{m-1}|X_m) \ldots f(X_1|X_2, \ldots X_m) \quad (4)$$

where, $f(X_l|X_{l+1}, \ldots X_{l+j-1})$: a conditional density of the random variable $X_l$ (for the $l^{th}$ dimension), where $1 \leq l \leq m-1$ and $j=m-l$.

By simplifying the equations 2 and 4, the joint density function f may be expressed in terms of univariate marginal density functions $f_1, f_2, \ldots f_m$ and bivariate copula densities as follows:

$$f(X_1, X_2, \ldots X_m) = \Pi_{k=1}^{m} f_k(X_k) \Pi_{j=1}^{m-1} \Pi_{l=1}^{m-j} c_{l,l+j|l+1, \ldots l+j-1}(F(X_l|X_{l+1}, \ldots X_{l+j-1}), F(X_{l+j}|X_{l+1}, \ldots X_{l+j-1})) \quad (5)$$

where, $c_{l,l+j|l+1, \ldots l+j-1}$: a density of a bivariate copula distribution $C_{l,l+j|l+1, \ldots l+j-1}$; and $F(X_l|X_{l+1}, \ldots X_{l+j-1})$: a conditional cumulative distribution of the random variable $X_l$.

A "bivariate copula distribution" refers to a copula distribution that may model a dependency between a pair of dimensions of a multivariate dataset. Examples of the bivariate copula distribution may include, but are not limited to, a T-student copula distribution, a Clayton copula distribution, a Gumbel copula distribution, or a Gaussian copula distribution. In an embodiment, the bivariate copula distribution may be a part of a D-vine copula distribution.

A "d-vine copula" refers to a hierarchal collection of bivariate copula distributions. In an embodiment, the d-vine copula may be represented graphically by a set of hierarchal trees, each of which may include a set of nodes arranged sequentially and connected by a set of edges. Further, each edge, connecting a pair of nodes in a hierarchal tree, may represent a bivariate copula distribution. In an embodiment, for "m" random variables, the d-vine copula may correspond to a hierarchal structure including m−1 hierarchal trees representing a total of $$\frac{m(m-1)}{2}$$

bivariate copula distributions. For example, a d-vine copula may be used to represent the bivariate copula distributions of the equation 5. In such a scenario, the variable j in the equation 5 may identify a hierarchal tree of the d-vine copula and the variable l in the equation 5 may identify an edge within that hierarchal tree, for representing each bivariate copula distribution of the equation 5 through the d-vine copula. In an embodiment, the d-vine copula may model a dependency between each pair of dimensions in a multivariate dataset. In an embodiment, the constituent bivariate copula distributions within the d-vine copula model may belong to different families of copula functions. Examples of the various families of copula functions include, but are not limited to, a T-student copula distribution, a Clayton copula distribution, a Gumbel copula distribution, or a Gaussian copula distribution.

An "h-function" refers to a conditional distribution of a random variable in terms of a bivariate copula distribution with known parameters. In an embodiment, the h-function may be used to represent an m-dimensional conditional distribution in terms of a pair of (m−1)-dimensional conditional distributions. Thus, the h-function may be used to recursively evaluate a conditional distribution in terms of individual random variables representing the various dimensions of the original conditional distribution. The following is a generic expression of a conditional cumulative distribution function represented in terms of an h-function:

$$F(X_j | X_1, \ldots X_{j-1}) = \qquad (6)$$
$$\frac{\delta C_{j,1|2,\ldots j-1}(F(X_j | X_2, \ldots X_{j-1}), F(X_1 | X_2, \ldots X_{j-1}))}{\delta F(X_1 | X_2, \ldots X_{j-1})} =$$
$$h(F(X_j | X_2, \ldots X_{j-1}), F(X_1 | X_2, \ldots X_{j-1})); \Sigma_{j,1|2 \ldots j-1}$$

where, $F(X_j|X_1, \ldots X_{j-1})$: a conditional cumulative distribution of $X_j$;

$c_{j, 1|2, \ldots, j-1}$: a bivariate copula distribution between $j^{th}$ and $1^{st}$ dimensions, conditioned on $2^{nd}$, $3^{rd}$, . . . $(j-1)^{th}$ parameters;

$\Sigma_{j, 1|2 \ldots, j-1}$: parameters of the bivariate copula distribution $C_{j, 1|2 \ldots j-1}$, which may be pre-estimated; and h( ): h function.

A person skilled in the art will understand that a conditional cumulative distribution of random variable may be equivalent to a conditional cumulative distribution of the corresponding marginal distribution of the random variable. Hence, an h-function in terms of the random variable may be equivalent to an h-function in terms of the corresponding marginal distribution of the random variable. For instance, $X_1$ and $X_2$ are random variables with corresponding marginal distributions $U_1=F_1(X_1)$ and $U_2=F_2(X_2)$. Then, $F(U_1|U_2)=F(X_1|X_2)=h(X_1, X_2)=h(U_1, U_2)$.

A "cumulative distribution" refers to a distribution function, that describes the probability that a real-valued random variable X with a given probability distribution will be found at a value less than or equal to x.

A "marginal cumulative distribution" refers to a cumulative distribution of a random variable representing a single dimension of a multivariate dataset. For example, $X_i$ is a random variable representing an $i^{th}$ dimension of the multivariate dataset. The marginal cumulative distribution of $X_i$ may be represented as $F_i(X_i)$ or $U_i$.

A "conditional cumulative distribution" refers to a multivariate cumulative distribution of multiple random variables, which is conditioned on at least one of the random variable. For example, $F(X_3|X_2, X_1)$ is a three-dimensional conditional cumulative distribution of random variables $X_1$, $X_2$, and $X_3$ such that the marginal cumulative distribution of the random variable $X_3$ may be conditioned on the marginal cumulative distributions of the random variables $X_1$ and $X_2$.

An "inverse cumulative distribution" refers to an inverse function of the cumulative distribution of the random variable X.

A "latent variable" refers to an intermediate or a transient variable that may not be directly obtainable from a multivariate dataset. In an embodiment, the latent variable may be determined based on one or more parameters of a distribution representing the multivariate dataset. For example, a latent variable (e.g., U) may be determined based on a marginal cumulative distribution (e.g., $F_i(X_i)$'s) of each dimension (e.g., $X_i$'s) in the multivariate dataset.

"Probability" shall be broadly construed, to include any calculation of probability; approximation of probability, using any type of input data, regardless of precision or lack of precision; any number, either calculated or predetermined, that simulates a probability; or any method step having an effect of using or finding some data that has some relation to a probability.

A "random variable" refers to a variable that may be assigned a value probabilistically or stochastically.

A "classifier" refers to a mathematical model that may be configured to categorize data into one or more categories. In an embodiment, the classifier is trained based on historical data. Examples of the classifier may include, but are not limited to, a Support Vector Machine (SVM), a Logistic Regression, a Bayesian Classifier, a Decision Tree Classifier, a Copula-based Classifier, a K-Nearest Neighbors (KNN) Classifier, or a Random Forest (RF) Classifier.

"Training" refers to a process of updating/tuning a classifier using a historical data such that the classifier is able to predict one or more categories in the historical data with a greater accuracy.

"Gibbs sampling" refers to a statistical technique that may be used to generate samples from a multivariate distribution. In an embodiment, Gibbs sampling corresponds to a Markov Chain Monte Carlo (MCMC) algorithm to obtain a sequence of observations from a joint distribution of two or more univariate marginal distributions, when direct sampling from the multivariate distribution may be difficult.

"Expectation Maximization (EM) algorithm" refers to a statistical technique of determining a Maximum Likelihood Estimate (MLE) of one or more parameters of a distribution, where the distribution depends on unobserved latent variables.

FIG. 1 is a block diagram illustrating a system environment 100 in which various embodiments may be implemented. The system environment 100 includes an application server 102, a database server 104, a human subject-computing device 106, and a network 112.

The application server 102 refers to a computing device, including one or more processors and one or more memories. The one or more memories may include computer readable code that is executable by the one or more processors to perform predetermined operation. In an embodiment, the predetermined operation may include predicting a health condition of a first human subject. In an embodiment, the application server 102 may extract a historical data comprising medical records of one or more second human subjects from the database server 104. In an embodiment, a medical record associated with a human subject may include a measure of one or more physiological parameters associated with the human subject.

In an embodiment, the application server 102 may generate a plurality of d-vines based on an estimation of one or more latent variables from a plurality of latent variables. Further, the application server 102 may train a classifier based on the generated plurality of d-vines.

In an embodiment, the application server 102 may predict a health condition of the first human subject. The application server 102 is configured to receive a measure of one or more physiological parameters associated with the first human subject. The one or more physiological parameters include at least one of an age, a cholesterol level, a heart rate, a blood pressure, a breath carbon-dioxide concentration, a breath oxygen concentration, a stroke score, a blood creatinine level, a blood albumin level, a blood sodium level, a total blood count, a blood glucose/sugar level, a blood hemoglobin level, and a blood platelet count. The application server 102 is configured to extract the historical data comprising the measure of the one or more physiological parameters associated with each of the one or more second human subjects. The application server 102 is configured to cluster the historical data into the plurality of d-vines by sampling the plurality of latent variables based on a rank transformation of the historical data by use of an extended rank likelihood technique. The application server 102 is configured to estimate the one or more latent variables from the plurality of latent variables based on a first count indicative of a number of the plurality of d-vines, a second count indicative of a number of the one or more records, a first value that is representative of a number of the one or more records clustered into a d-vine from the plurality of d-vines, and a second value that is representative of a parameter utilizable to predict a third value. The third value corresponds to a probability of clustering the historical data into the d-vine from the plurality of d-vines. The application server 102 is configured to generate the plurality of d-vines based on the estimated one or more latent variables from the plurality of latent variables. The application server 102 is further configured to train the classifier based on the generated plurality of d-vines. The training of the classifier based on the d-vine copula distribution has been explained further in conjunction with FIG. 3. The application server 102 is furthermore configured to predict the health condition of the first human subject by utilizing the classifier based on the received measure of the one or more physiological parameters associated with the first human subject.

Thereafter, based on the measure of the one or more physiological parameters of the first human subject, the application server 102 may predict the health condition of the first human subject using the classifier. The application server 102 may then display the predicted health condition of the first human subject through a user-interface on the human subject-computing device 106. The prediction of the health condition of the first human subject has been explained further in conjunction with FIG. 4.

The application server 102 may be realized through various types of application servers such as, but not limited to, Java application server, .NET framework application server, and Base4 application server.

The database server 104 may refer to a computing device, which stores at least the historical data including the medical records of the one or more second human subjects. In addition, in an embodiment, the database server 104 may also store the one or more physiological parameters of the first human subject, which may be received from the human-subject computing device 106 of the first human subject. In an embodiment, the database server 104 may receive a query from the application server 102 to extract the information stored on the database server 104. The database server 104 may be realized through various technologies such as, but not limited to, Oracle®, IBM DB2®, Microsoft SQL Server®, Microsoft Access®, PostgreSQL®, MySQL® and SQLite®, and the like. In an embodiment, the application server 102 may connect to the database server 104 using one or more protocols such as, but not limited to, Open Database Connectivity (ODBC) protocol and Java Database Connectivity (JDBC) protocol.

A person with ordinary skill in the art will understand that the scope of the disclosure is not limited to the database server 104 as a separate entity. In an embodiment, the functionalities of the database server 104 can be integrated into the application server 102.

The human subject-computing device 106 refers to a computing device used by a human subject (such as the first human subject and the one or more second human subjects). The human subject-computing device 106 may include one or more processors and one or more memories. The one or more memories may include computer readable code that is executable by the one or more processors to perform predetermined operation. In an embodiment, one or more biosensors (e.g., a biosensor-1 108a, a biosensor-2 108b, and a biosensor-3 108c) may be inbuilt within the human subject-computing device 106. Alternatively, the one or more biosensors (e.g., a biosensor-1 108a, a biosensor-2 108b, and a biosensor-3 108c) may be coupled to the human subject-computing device 106 through one or more data acquisition (DAQ) interfaces (e.g., a DAQ interface-1 110a, a DAQ interface-2 110b, and a DAQ interface-3 110c). For instance, as shown in FIG. 1, the DAQ interface-1 110a may connect the biosensor-1 108a with the human subject-computing device 106. Similarly, the DAQ interface-2 110b may connect the biosensor-2 108b with the human subject-computing device 106, and so on. In another embodiment, the one or more biosensors, for example, 108a, may be connected to the human subject-computing device 106 through a wireless connection such as, but not limited to, a Bluetooth based connection, a Near Field Communication (NFC) based connection, a Radio Frequency Identification (RFID) based connection, or any other wireless communication protocol.

In an embodiment, the one or more biosensors (e.g., 108a-108c) may refer to DAQ devices that can be used to gather various signals from a human subject and generate corresponding readings of the one or more physiological parameter of the human subject. Examples of the one or more physiological parameters include, but are not limited to, an age, a cholesterol level, a heart rate, a blood pressure, a breath carbon-dioxide concentration, a breath oxygen concentration, a stroke score, a blood creatinine level, a blood albumin level, a blood sodium level, a total blood count, a blood glucose/sugar level, a blood hemoglobin level, and a blood platelet count. In an embodiment, the one or more biosensors (e.g., 108a-108c) may be attached to a body of the human subject to measure the one or more physiological parameters of the human subject. Examples of such biosensors include, but are not limited to, a blood pressure/pulse sensor, or a temperature sensor. Alternatively, the one or more biosensors (e.g., 108a-108c) may correspond to one or more blood sample analyzers for analyzing a blood sample taken from the human subject to determine readings of one or more blood tests. In another embodiment, the one or more biosensors (e.g., 108a-108c) may correspond to one or more breath analyzers for analyzing a breath sample of the human subject.

In an embodiment, the one or more DAQ interfaces (e.g., 110a-110c) may connect the one or more biosensors (e.g., 108a-108c) with the human-subject computing device 106. Further, the one or more DAQ interfaces (e.g., 110a-110c) may facilitate communication between each of the one or more biosensors (e.g., 108a-108c) and the human-subject computing device 106. In an embodiment, to facilitate communication between a biosensor (e.g., 108a) in the one or more biosensors (e.g., 108a-108c) and the human-subject computing device 106 connected through a respective DAQ interface (e.g., 110a), the respective DAQ interface (e.g., 110a) may convert a signal of a first format, generated by the biosensor (e.g., 108a), to a signal of a second format, acceptable by the human-subject computing device 106, and vice versa. For instance, the DAQ interface (e.g., 110a) may convert analogue signals generated by the biosensor (e.g., 108a) to corresponding digital signals, acceptable by the human-subject computing device 106. Further, the DAQ interface (e.g., 110a) may serialize or parallelize the digital signals in accordance with data-input requirements of the human-subject computing device 106. For instance, the DAQ interface (e.g., 110a) may parallelize digital signals into 32-bit data words if the human-subject computing device 106 accepts digital data in a 32-bit format. Examples of the DAQ interface include, but are not limited to, a Universal Serial Bus (USB) Port, a FireWire Port, an IEEE 1394 standard based connector, or any other serial/parallel data interfacing connector known in the art.

In an embodiment, the human subject-computing device 106 may transmit the measure of the one or more physiological parameters of the human subject to at least one of the application server 102 or the database server 104. In an embodiment, the application server 102 may predict a health condition of the human subject, as described above. Thereafter, the human subject-computing device 106 may display the predicted health condition of the human subject through a user-interface on a display device of the human subject-computing device 106. Based on the predicted health condition of the human subject, the human subject may consult with a medical practitioner.

A person skilled in the art will understand that the scope of the disclosure is not limited to the human subject-computing device 106 being used by the human subject. In an embodiment, the human subject-computing device 106 may be used by a medical practitioner. In such a scenario, when a human subject visits the medical practitioner for a consultation, the medical practitioner may use the human subject-computing device 106 to measure the one or more physiological parameters of the human subject. Thereafter, the human subject-computing device 106 may transmit the one or more physiological parameters of the human subject to at least one of the application server 102 or the database server 104. The application server 102 may predict a health condition of the human subject, as described above. Thereafter, the human subject-computing device 106 may display the predicted health condition of the human subject through the user-interface on a display device of the human subject-computing device 106. Based on the predicted health condition of the human subject, the medical practitioner may recommend a treatment course, including one or more medicines, one or more clinical/pathological tests, or one or more diet plans to the human subject.

The human subject-computing device 106 may include a variety of computing devices such as, but not limited to, a laptop, a personal digital assistant (PDA), a tablet computer, a smartphone, a phablet, and the like.

A person skilled in the art will understand that the scope of the disclosure is not limited to the human subject-computing device 106 and the application server 102 as separate entities. In an embodiment, the application server 102 may be realized as an application hosted on or running on the human subject-computing device 106 without departing from the spirit of the disclosure.

The network 112 corresponds to a medium through which content and messages flow between various devices of the system environment 100 (e.g., the application server 102, the database server 104, and the human subject-computing device 106). Examples of the network 112 may include, but are not limited to, a Wireless Fidelity (Wi-Fi) network, a Wireless Area Network (WAN), a Local Area Network (LAN), or a Metropolitan Area Network (MAN). Various devices in the system environment 100 can connect to the network 112 in accordance with various wired and wireless communication protocols such as Transmission Control Protocol and Internet Protocol (TCP/IP), User Datagram Protocol (UDP), and 2G, 3G, or 4G communication protocols.

Figure 2:
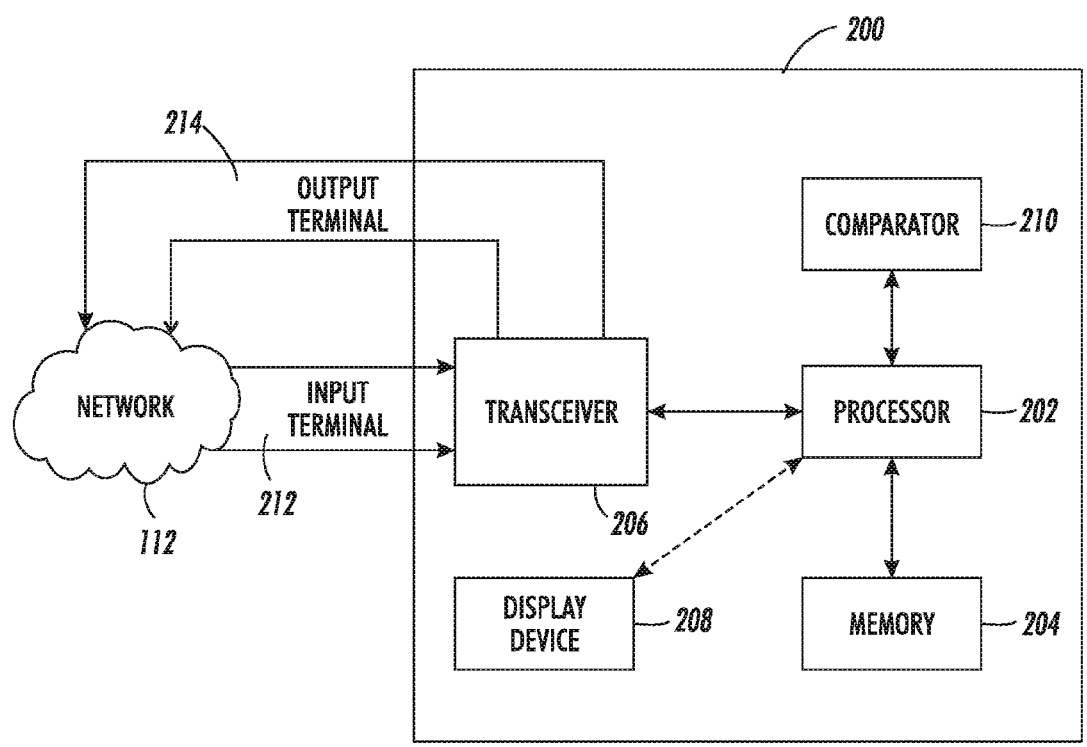
FIG. 2 is a block diagram of a system that is capable of predicting health condition of a first human subject, in accordance with at least one embodiment.

FIG. 2 is a block diagram of a system 200 that is capable of predicting health condition of the first human subject, in accordance with at least one embodiment. In an embodiment, the system 200 may correspond to the application server 102 or the human subject-computing device 106. For the purpose of ongoing description, the system 200 is considered the application server 102. However, the scope of the disclosure should not be limited to the system 200 as the application server 102. The system 200 may also be realized as the human subject-computing device 106, without departing from the spirit of the disclosure.

The system 200 includes a processor 202, a memory 204, a transceiver 206, a display 208, and a comparator 210. The processor 202 is coupled to the memory 204 and the transceiver 206. The transceiver 206 is coupled to a network 112 through an input terminal 212 and an output terminal 214.

The processor 202 includes suitable logic, circuitry, and interfaces and is configured to execute one or more instructions stored in the memory 204 to perform predetermined operations on the computing device 100. The memory 204 may be configured to store the one or more instructions. The processor 202 may be implemented using one or more processor technologies known in the art. Examples of the processor 202 include, but are not limited to, an X86 processor, a RISC processor, an ASIC processor, a CISC processor, or any other processor.

The memory 204 stores a set of instructions and data. Some of the commonly known memory implementations include, but are not limited to, a RAM, a read-only memory (ROM), a hard disk drive (HDD), and a secure digital (SD) card. Further, the memory 204 includes the one or more instructions that are executable by the processor 202 to perform specific operations. It is apparent to a person having ordinary skill in the art that the one or more instructions stored in the memory 204 enable the hardware of the computing device 100 to perform the predetermined operations.

The transceiver 206 transmits and receives messages and data to/from one or more computing devices connected to the computing device 100 over the network 112. Examples of the network 112 may include, but are not limited to, a Wireless Fidelity (Wi-Fi) network, a Wireless Area Network (WAN), a Local Area Network (LAN), or a Metropolitan Area Network (MAN). In an embodiment, the transceiver 206 is coupled to the network 112 through the input terminal 212 and the output terminal 214, through which the transceiver 206 may receive and transmit data/messages, respectively. Examples of the transceiver 206 may include, but are not limited to, an antenna, an Ethernet port, a USB port, or any other port that can be configured to receive and transmit data. The transceiver 206 transmits and receives data/messages in accordance with the various communication protocols such as, TCP/IP, UDP, and 2G, 3G, or 4G communication protocols.

The display 208 facilitates a user of the computing device 100 to view information presented on the computing device 100. For example, the user may view information associated with the predicted health condition of the first human subject on the display 208. The display 208 may be realized through several known technologies, such as Cathode Ray Tube (CRT) based display, Liquid Crystal Display (LCD), Light Emitting Diode (LED) based display, Organic LED based display, and Retina display® technology. In an embodiment, the display 208 can be a touch screen that is operable to receive a user-input.

The comparator 210 is configured to compare at least two input signals to generate an output signal. In an embodiment, the output signal may correspond to either "1" or "0." In an embodiment, the comparator 210 may generate output "1" if the value of a first signal (from the at least two signals) is greater than the value of a second signal (from the at least two signals). Similarly, the comparator 210 may generate an output "0" if the value of the first signal is less than the value of the second signal. In an embodiment, the comparator 210 may be realized through either software technologies or hardware technologies known in the art. Though, the comparator 210 is depicted as independent from the processor 202 in FIG. 1, a person skilled in the art will appreciate that the comparator 210 may be implemented within the processor 202 without departing from the scope of the disclosure.

Figure 3:
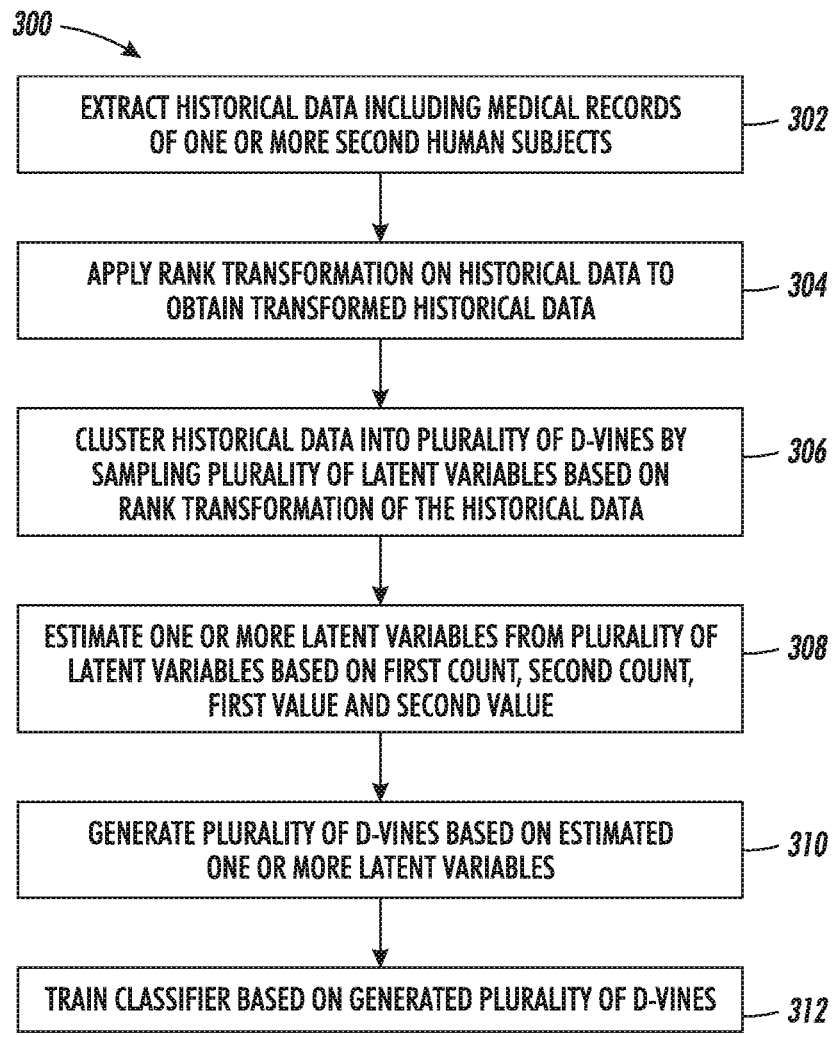
FIG. 3 illustrates a flowchart of a method for training a classifier based on the generated plurality of d-vines, in accordance with at least one embodiment.

An embodiment of operation of the system 200 for training of the classifier based on the generated plurality of d-vines has been explained further in conjunction with FIG. 3. The prediction of a health condition of the first human subject using the trained classifier has been explained in conjunction with FIG. 4.

FIG. 3 illustrates a flowchart 300 of a method for training the classifier based on the generated plurality of d-vines, in accordance with at least one embodiment. The flowchart 300 has been described in conjunction with FIG. 1 and FIG. 2.

At step 302, the historical data including medical records of the one or more second human subjects is extracted. In an embodiment, the processor 202 is configured to extract the historical data from the database server 104.In a scenario where the historical data is stored in the memory 204, the processor 202 may extract the historical data from the memory 204. In an embodiment, the historical data may correspond to a multivariate dataset from which health condition of a human subject may be identifiable based on generation of the plurality of d-vines. Further, the data type associated with the historical data corresponds to at least one of a numerical data type or a categorical data type.

In an embodiment, the historical data may correspond to a multivariate healthcare dataset, which includes a measure of the one or more physiological parameters of each of the one or more second human subjects. Examples of the one or more physiological parameters include, but are not limited to, an age, a cholesterol level, a heart rate, a blood pressure, a breath carbon-dioxide concentration, a breath oxygen concentration, a stroke score, a blood creatinine level, a blood albumin level, a blood sodium level, a total blood count, a blood glucose/sugar level, a blood hemoglobin level, and a blood platelet count. In an embodiment, the historical data may correspond to an m-dimensional multivariate dataset, where the one or more physiological parameters correspond to dimensions of the multivariate healthcare dataset. Thus, each physiological parameter may correspond to a different dimension in the m-dimensional multivariate dataset corresponding to the historical data. Further, each medical record in the historical data may correspond to an observation in the m-dimensional multivariate dataset corresponding to the historical data.

A person having ordinary skill in the art will understand that the scope of disclosure is not limited to the aforementioned one or more physiological parameters. In an embodiment, various other physiological parameters may be used without departing from the spirit of the disclosure.

At step 304, the rank transformation is applied on the historical data to obtain a transformed historical data. In an embodiment, the processor 202 is configured to obtain the transformed historical data by applying the rank transformation on the historical data using the extended rank likelihood technique. To generate the transformed historical data, the processor 202 determines ranks of the individual observations in each of the p-dimensions in the historical data. In an embodiment, the processor 202 may assign a rank 1 to an observation having the highest value among the other observations in a particular dimension. Further, the processor 202 may assign a rank 2 to an observation having the next highest value in that dimension, and so on until a rank N is assigned to an observation having the lowest value in the particular dimension in the historical data. Thereafter, in an embodiment, the processor 202 may divide each rank by N so that the final values of the ranks of the observations lie between 0 and 1. The final values of the ranks of the observations, which lie between 0 and 1, may correspond to the transformed historical data. For example, the historical data includes five observations. The values of the five observations for a particular dimension may include the values 0.1, 5.6, 3.1, 0.8, and 2.2. The processor 202 may assign the ranks 1, 5, 4, 2, and 3 to the observations. Further, the processor 202 may determine the final values of the ranks, and hence the transformed historical data as 0.2, 1, 0.8, 0.4, and 0.6 (i.e., by dividing the ranks by 5).

A person skilled in the art will appreciate that the historical data may include data of various data types such as, but not limited to, a numerical data type or a categorical data type. For instance, a first set of these physiological parameters may be represented using a continuous data type, while a second set of physiological parameters from the one or more physiological parameters may be of a discrete data type. However, in an embodiment, the transformed historical data may include only the ranks. Further, the transformed historical data may not have any missing values, even in a scenario where the historical data has certain missing values. In an embodiment, a bivariate copula distribution determined from the original historical data may be same as a bivariate copula distribution determined from the transformed historical data. As the transformed multivariate dataset does not include any missing values or categorical data, the bivariate copula distribution determined from the transformed historical data may be more accurate in identifying one or more clusters in the historical data (e.g., one or more health conditions of the second human subjects) than the bivariate copula distribution determined from the original historical data, which may have missing values or categorical data.

For example, the historical data includes a physiological parameter such as gender, which is of a categorical data type. Thus, observations for the physiological parameter "gender" may have either a value of "Male" or "Female", which in turn may be represented as "0" and "1" in the historical data. In an embodiment, the processor 202 may determine a binomial distribution of the observations of gender in the historical data. Thereafter, the processor 202 may fit the binomial distribution to a Gaussian distribution based on the rank transformation. Thus, the observations of categorical data type in the historical data may be converted into numerical data in the transformed historical data. Further, a missing value $u_{ij}$ in the historical data may be imputed based on an inverse transform sampling of a random variable $X_j$ (for the $j^{th}$ physiological parameter).

The rank transformed historical data may be clustered into the plurality of d-vines, as explained next. At step 306, the historical data is clustered into the plurality of d-vines by sampling the plurality of the latent variables based on the rank transformation of the historical data. In an embodiment, the processor 202 may be configured to perform clustering of the rank transformed historical data into the plurality of d-vines by sampling of the plurality of latent variables. In an embodiment, a d-vine may model a dependency between each pair of physiological parameters from the one or more physiological parameters. The processor 202 may cluster the rank transformed historical data by assigning a first data set (including certain number of data points from the rank transformed historical data) to a first d-vine, a second data set (from the rank transformed historical data) to a second d-vine, and so on, based on the plurality of sampled latent variables.

The process of sampling $U_j^i$ from its truncated condition CDF to ensure the condition $U_j^i \in H_j^i$ is satisfied, by inverting its conditional CDF using evaluations of the inverse of h function. Following is a pseudo-code for sampling the latent variables. The pseudo-code is represented as under:

for each j=1, . . . , M do
$U_{j,L}^i=\max_l\{U^l:X_j^i<y\}$
$U_{j,H}^i=\min_l\{U_j^i:y<X_j^i\}$
if j==1 then
$U_1^i \sim$ uni f $(U_{j,L}^i, U_{j,H}^i)$
else
$R^{low}=F(U_{j,L}^i|U_1^i, \ldots U_{j-1}^i)$
$R^{high}=F(U_{j,H}^i|U_1^i, \ldots U_{j-1}^i)$
R~uni f $(R^{low}, R^{high})$
for t in 2:j−1 do
$R=h^{-1}(R, F(U_{t-1}^i|U_t^i, \ldots, U_{j-1}^i)$
$U_j^i=h^{-1}(R, U_{j-1}^i)$ The clustering method models the data as a mixture of d-Vines to be used as the extended rank likelihood framework to estimate the parameters of the mixture of d-Vines. Following is a pseudo-code of a generative model for the d-vine mixture. The pseudo-code is represented as under:

for k=1 to k do
for j=1 to M−1 do
for l=1 to $M_{-j}$ do
//Sample the parameters of bivariate copulas from their prior $\Sigma k, j, l+1|l+1, \ldots, l+j-1$~Inverse-Wishart $(v_0, V_0)$ $\emptyset$~Dir($\infty$)
for each i=1, . . . ,N//Each data point do
$Y^i$~Mult($\emptyset$)
$U^i|Y^i=k$~DVineUnif($\Sigma k$)
//Where $\Sigma k=\{\Sigma k, l, j+1|l+1, \ldots, l+j-1:1\leq j\leq M-1, 1\leq l\leq M-j\}$
for each j=1 to, . . . ,M //For each dimension do $X_j^i=F_j^{-1}(U_j^i)$ At step 308, the one or more latent variables from the plurality of latent variables are estimated based on the first count, the second count, the first value, and the second value. The first count indicative of the number of the plurality of d-vines. The second count indicative of the number of the one or more records. The first value that is representative of the number of the one or more records clustered into a d-vine from the plurality of d-vines. The second value that is representative of a parameter utilizable to predict the third value, wherein the third value corresponds to the probability of clustering the historical data into the d-vine from the plurality of d-vines.

The latent variables in the d-vine mixture model include the parameters, U variables, Y variables and θ. The d-vine mixture model conjugating the Dirichlet prior to θ and further collapsing θ, leads to faster mixing. Hence, this leaves to sampling the parameters, the U variables and the Y variables by summation. Let the number of data points assigned to a particular cluster k. The rank likelihood based inference algorithm is summarized in the following algorithm. This rank likelihood based approach allows estimating the parameters without any assumption on the marginal and handles both continuous and discrete data. Following is a pseudo-code to Gibbs sampling scheme for rank likelihood based estimation of mixture of d-vines. The pseudo-code is represented as under:

For each i=1, . . . N do $$\text{Sample } p(Y^i = k | U, \Sigma) \propto \frac{n_k + \alpha}{N + k\alpha}$$

For each i=1, . . . N do
For each j=1, . . . M do
  Let k=$Y^i$ $U_{j,L}^i=\max_l\{U_j^i:X_j^i<y, Y^l=k\}$ $U_{j,H}^i=\min_i\{U_j^i: y<X_j^i, Y^l=k\}$ $U_j^i \sim p(U_j^i|\Sigma, U_1^i, \ldots, U_{j-1}^i, U^{-i}, U_{j,L}^i \leq U_j^i \leq U_{j,H}^i)$ ////Where $\Sigma$, is the set of covariance matrices of all the bivariate copulas Construct all the U variables
for k=1 to K do
for j=1 to M−1 do
for l=1 to M=j do
//The parameters of the first level bivariate copulas depend on pairs of sampled marginal variables. The parameters of the higher level bivariate copulas (j>1) depend on the higher order conditionals, and pairs of $\bar{U}$ variables. To construct the posterior for each parameter in $\Sigma$, with the inverse Wishart prior, we therefore construct a matrix W ($n_k$* 2 matrix)with columns as specified below, where $S_k=\{1\leq i \leq N: Y^i=k\}$
if j==1 then
$W^1=U_l^{Sk}, W_2=U_{1+j}^{Sk}$
else
$W_1=\bar{U}_{l|l+1, \ldots, l+j-1}^{S_k}, W_2^{Sk}=\bar{U}_{l+j|l+1, \ldots, l+j-1}^{S_k}$ $\Sigma k, l, j+1|l+1, \ldots, l+j-1$~Inverse-Wishart($v_o+n, v_o V_o+W^T W$)

In an embodiment, the one or more latent variables include one or more parameters associated with each of the plurality of d-vines, a cumulative distribution of each of the one or more physiological parameters, or a distribution of the one or more records into each of the plurality of d-vines.

In an embodiment, the one or more parameters associated with each of the plurality of d-vines are estimated by utilizing one of a Gibbs sampling technique or an Expectation-Maximization (EM) technique. In an embodiment, the one or more parameters comprise at least a covariance matrix associated with the d-vine from the plurality of d-vines.

At step 310, the plurality of d-vines are generated based on the estimated one or more latent variables from the plurality of latent variables. At step 312, a classifier is trained based on the generated plurality of d-vines.

A person skilled in the art will appreciate that the scope of the disclosure is not limited to the training of the classifier, as discussed above. The classifier may be trained using any machine learning or artificial intelligence technique known in the art without departing from the spirit of the disclosure.

A person having ordinary skills in the art will understand that the scope of the disclosure is not limited to the prediction of the health condition of the first human subject based on above mentioned sequence of steps as described flowchart 300. The above mentioned sequence of steps of the flowchart 300 may be executed or processed in any sequence to predict the health condition of the first human subject without limiting the scope of the disclosure.

Figure 4:
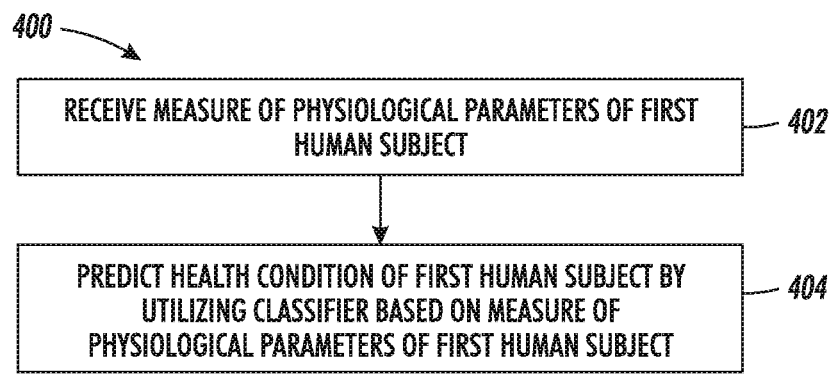
FIG. 4 illustrates a flowchart of a method for predicting a health condition of a first human subject, in accordance with at least one embodiment.

FIG. 4 illustrates a flowchart 400 of a method for predicting a health condition of a first human subject, in accordance with at least one embodiment.

At step 402, a measure of the one or more physiological parameters of the first human subject is received. In an embodiment, the processor 202 is configured to receive the measure of the one or more physiological parameters of the first human subject from the human subject-computing device 106 of the first human subject. In an embodiment, as discussed, the one or more biosensors, for example, 108a, may be inbuilt within the human subject-computing device 106. Alternatively, the one or more biosensors, for example, 108a may be coupled to the human subject-computing device 106 through the one or more DAQ interfaces, for example, 110a. In an embodiment, the one or more biosensors, for example, 108a, may measure the one or more physiological parameters of the first human subject. Thereafter, the human subject-computing device 106 may send the one or more physiological parameters of the first human subject to the processor 202.

At step 404, the health condition of the first human subject is predicted using the classifier. In an embodiment, the processor 202 is configured to predict the health condition of the first human subject using the classifier. Prior to predicting the health condition, the processor 202 may receive a measure of the one or more physiological parameters of the first human subject from the user. Based on the one or more physiological parameters of the first human subject, the processor 202 may predict the health condition of the first human subject by utilizing the classifier. Further, the processor 202 may display the predicted health condition of the first human subject through a user-interface on the human subject-computing device 106 of the first human subject. In an embodiment, the health condition may correspond to at least one of a disease risk, a disease symptom, an onset of a disease, a recovery from a disease, or an effect of medications for a disease.

A person having ordinary skill in the art will understand that the scope of the disclosure should not be limited to determining a health condition of a human subject. In an embodiment, similar medical data may be analyzed to draw out various inferences. For instance, insurance data pertaining to health care may be analyzed to determine health insurance frauds.

Further, the disclosure may be implemented for analysis of data from various levels of the healthcare industry such as at individual patient level through analysis of Electronic Medical Records (EMR), or at hospital level (e.g., identifying a group of patients having risk of getting involved in health insurance frauds). For example, the historical data may correspond to a multivariate dataset, including medical insurance records of one or more individuals. In such a scenario, the p-dimensional variable in each medical insurance record may correspond to one or more insurance related parameters such as age of an insured person, one or more physiological parameters of the insured person, premium being paid by the insured person, insurance amount, coverage limit, and so on. Thus, the process described in the flowchart 300 may be utilized to determine insurance frauds, recommend insurance amounts, etc.

Further, a person skilled in the art will appreciate that the scope of the disclosure should not be limited to predicting the health condition of the first human subject. In an embodiment, the disclosure may be implemented for identifying one or more categories in any multivariate dataset. Further, the disclosure may be implemented for predicting a category from the one or more categories into which a new record of the multivariate dataset may be classified. For example, the disclosure may be implemented to analyze a financial dataset to determine a credit risk category of a customer. Further, the financial dataset may be analyzed to categorize the customers in one or more categories of buying behaviors. The financial dataset may include various types of financial data such as, but not limited to, loan risk assessment data, insurance data, bank statements, and bank transaction data.

The disclosed embodiments encompass numerous advantages. The disclosure leads to an effective clustering of a multivariate dataset using a d-vine copula distribution model for effective handling of mixed data types. For example, the multivariate dataset may be a healthcare dataset that includes medical records of one or more human subjects. By using the d-vine copula, one or more clusters indicative of one or more health conditions of the one or more human subjects may be identified. The d-vine copula, though a very robust statistical method for clustering data of a numerical data type, may be inefficient while handling data of a categorical data type. Further, the d-vine copula may not perform well in case of missing values in the multivariate dataset. In addition, the sampling of latent variables for determining the d-vine copula may be a non-trivial task. The disclosure overcomes the aforementioned shortcomings of the d-vine copula for clustering the multivariate dataset and determining of complex dependencies within the multivariate dataset.

The disclosed methods and systems, as illustrated in the ongoing description or any of its components, may be embodied in the form of a computer system. Typical examples of a computer system include a general-purpose computer, a programmed microprocessor, a micro-controller, a peripheral integrated circuit element, and other devices or arrangements of devices that are capable of implementing the steps that constitute the method of the disclosure.

The computer system comprises a computer, an input device, a display unit and the Internet. The computer further comprises a microprocessor. The microprocessor is connected to a communication bus. The computer also includes a memory. The memory may be Random Access Memory (RAM) or Read Only Memory (ROM). The computer system further comprises a storage device, which may be a hard-disk drive or a removable storage drive, such as, a floppy-disk drive, optical-disk drive, and the like. The storage device may also be a means for loading computer programs or other instructions into the computer system. The computer system also includes a communication unit. The communication unit allows the computer to connect to other databases and the Internet through an input/output (I/O) interface, allowing the transfer as well as reception of data from other sources. The communication unit may include a modem, an Ethernet card, or other similar devices, which enable the computer system to connect to databases and networks, such as, LAN, MAN, WAN, and the Internet. The computer system facilitates input from a user through input devices accessible to the system through an I/O interface.

In order to process input data, the computer system executes a set of instructions that are stored in one or more storage elements. The storage elements may also hold data or other information, as desired. The storage element may be in the form of an information source or a physical memory element present in the processing machine.

The programmable or computer-readable instructions may include various commands that instruct the processing machine to perform specific tasks, such as steps that constitute the method of the disclosure. The systems and methods described can also be implemented using only software programming or using only hardware or by a varying combination of the two techniques. The disclosure is independent of the programming language and the operating system used in the computers. The instructions for the disclosure can be written in all programming languages including, but not limited to, "C,""C++,""Visual C++" and "Visual Basic." Further, the software may be in the form of a collection of separate programs, a program module containing a larger program or a portion of a program module, as discussed in the ongoing description. The software may also include modular programming in the form of object-oriented programming. The processing of input data by the processing machine may be in response to user commands, the results of previous processing, or from a request made by another processing machine. The disclosure can also be implemented in various operating systems and platforms including, but not limited to, "Unix", "DOS", "Android", "Symbian", and "Linux."

The programmable instructions can be stored and transmitted on a computer-readable medium. The disclosure can also be embodied in a computer program product comprising a computer-readable medium, or with any product capable of implementing the above methods and systems, or the numerous possible variations thereof.

Various embodiments of methods and systems for predicting health condition of a human subject have been disclosed. However, it should be apparent to those skilled in the art that modifications in addition to those described, are possible without departing from the inventive concepts herein. The embodiments, therefore, are not restrictive, except in the spirit of the disclosure. Moreover, in interpreting the disclosure, all terms should be understood in the broadest possible manner consistent with the context. In particular, the terms "comprises" and "comprising" should be interpreted as referring to elements, components, or steps, in a non-exclusive manner, indicating that the referenced elements, components, or steps may be present, or utilized, or combined with other elements, components, or steps that are not expressly referenced.

A person having ordinary skills in the art will appreciate that the system, modules, and sub-modules have been illustrated and explained to serve as examples and should not be considered limiting in any manner. It will be further appreciated that the variants of the above disclosed system elements, or modules and other features and functions, or alternatives thereof, may be combined to create other different systems or applications.

Those skilled in the art will appreciate that any of the aforementioned steps and/or system modules may be suitably replaced, reordered, or removed, and additional steps and/or system modules may be inserted, depending on the needs of a particular application. In addition, the systems of the aforementioned embodiments may be implemented using a wide variety of suitable processes and system modules and is not limited to any particular computer hardware, software, middleware, firmware, microcode, or the like.

The claims can encompass embodiments for hardware, software, or a combination thereof.

It will be appreciated that variants of the above disclosed, and other features and functions or alternatives thereof, may be combined into many other different systems or applications. Presently unforeseen or unanticipated alternatives, modifications, variations, or improvements therein may be subsequently made by those skilled in the art, which are also intended to be encompassed by the following claims.

What is claimed is:

1. A method of operating a health condition profiling system,
the method comprising:
receiving, by processors said transceiver, a measure of one or more physiological parameters associated with a first human subject, wherein the one or more physiological parameters comprise at least one of an age, a cholesterol level, a heart rate, a blood pressure, a breath carbon-dioxide concentration, a breath oxygen concentration, a stroke score, a blood creatinine level, a blood albumin level, a blood sodium level, a total blood count, a blood glucose/sugar level, a blood hemoglobin level, and/or a blood platelet count;
extracting, by the one or more processors, a historical data comprising one or more records, wherein each of the one or more records includes a measure of the one or more physiological parameters associated with each of one or more second human subjects, wherein the historical data is missing values, comprises categorical data, or both;
clustering, by the one or more processors, the historical data into a plurality of d-vines by sampling a plurality of latent variables based on a rank transformation of the historical data, wherein the transformed historical data does not include any missing values or categorical data;
estimating, by the one or more processors, one or more latent variables from the plurality of latent variables based on:
a first count indicative of a number of the plurality of d-vines,
a second count indicative of a number of the one or more records,
a first value that is representative of a number of the one or more records clustered into a d-vine from the plurality of d-vines, and
a second value that is representative of a parameter utilizable to predict a third value, wherein the third value corresponds to a probability of clustering the historical data into the d-vine from the plurality of d-vines;
generating, by the one or more processors, the plurality of d-vines based on the estimated one or more latent variables from the plurality of latent variables;
training, by the one or more processors, a classifier based on the generated plurality of d-vines, the classifier configured to sort data into one or more health condition categories, each health condition category corresponding to a health condition, wherein the historical data corresponds to a multivariate dataset from which the health condition is identifiable based on the generated plurality of d-vines;
sorting, by the one or more processors, the received measure of the one or more physiological parameters associated with the first human subject into one or more of the health condition categories using the trained classifier;
assigning, by the one or more processors, a health condition profile to the first human subject, the profile comprising one or more health conditions corresponding to the one or more categories into which the measure is sorted; and
displaying the health condition profile on the display device.

2. The method of claim 1, wherein the one or more latent variables include one or more parameters associated with each of the plurality of d-vines, a cumulative distribution of each of the one or more physiological parameters, or a distribution of the one or more records into each of the plurality of d-vines.

3. The method of claim 2, wherein the one or more parameters associated with each of the plurality of d-vines are estimated by utilizing one of a Gibbs sampling technique or an Expectation-Maximization (EM) technique.

4. The method of claim 2, wherein the one or more parameters associated with each of the plurality of d-vines are estimated based on an inverse Wishart distribution.

5. The method of claim 2, wherein the one or more parameters comprise at least a covariance matrix associated with the d-vine from the plurality of d-vines.

6. The method of claim 1, wherein the d-vine from the plurality of d-vines models a dependency between each pair of physiological parameters from the one or more physiological parameters, wherein a first set of physiological parameters from the one or more physiological parameters are continuous and a second set of physiological parameters from the one or more physiological parameters are discrete.

7. The method of claim 1, wherein the rank transformation corresponds to an extended rank likelihood technique.

8. The method of claim 1, wherein the health condition corresponds to at least one of a disease risk, a disease symptom, an onset of a disease, a recovery from a disease, or an effect of medications for a disease.

9. A health condition profiling system comprising a display device and an application server, the application server comprising:
a transceiver configured to receive a measure of one or more physiological parameters associated with a first human subject, wherein the one or more physiological parameters comprise at least one of an age, a cholesterol level, a heart rate, a blood pressure, a breath carbon-dioxide concentration, a breath oxygen concentration, a stroke score, a blood creatinine level, a blood albumin level, a blood sodium level, a total blood count, a blood glucose/sugar level, a blood hemoglobin level, and/or a blood platelet count, and one or more processors configured to:
extract a historical data comprising one or more records, wherein each of the one or more records includes a measure of the one or more physiological parameters associated with each of one or more second human subjects, wherein the historical data is missing values, comprises categorical data, or both;
cluster the historical data into a plurality of d-vines by sampling a plurality of latent variables based on a rank transformation of the historical data, wherein the transformed historical data does not include any missing values or categorical data;
estimate one or more latent variables from the plurality of latent variables based on:
a first count indicative of a number of the plurality of d-vines,
a second count indicative of a number of the one or more records,
a first value that is representative of a number of the one or more records clustered into a d-vine from the plurality of d-vines, and
a second value that is representative of a parameter utilizable to predict a third value, wherein the third value corresponds to a probability of clustering the historical data into the d-vine from the plurality of d-vines;
generate the plurality of d-vines based on the estimated one or more latent variables from the plurality of latent variables;
train a classifier based on the generated plurality of d-vines, the classifier configured to sort data into one or more health condition categories, each health condition category corresponding to a health condition, wherein the historical data corresponds to a multivariate dataset from which the health condition is identifiable based on the generated plurality of d-vines;
sort the received measure of the one or more physiological parameters associated with the first human subject into one or more of the health condition categories using the trained classifier;
assign, by the one or more processors, a health condition profile to the first human subject, the profile comprising one or more health condition corresponding to the one or more categories into which the measure is sorted; and
display the health condition on the display device.

10. The application server of claim 9, wherein the one or more latent variables include one or more parameters associated with each of the plurality of d-vines, a cumulative distribution of each of the one or more physiological parameters, or a distribution of the one or more records into each of the plurality of d-vines.

11. The application server of claim 10, wherein the one or more parameters associated with each of the plurality of d-vines are estimated by utilizing one of a Gibbs sampling technique or an Expectation-Maximization (EM) technique.

12. The application server of claim 10, wherein the one or more parameters associated with each of the plurality of d-vines are estimated based on an inverse Wishart distribution.

13. The application server of claim 10, wherein the one or more parameters comprise at least a covariance matrix associated with the d-vine from the plurality of d-vines.

14. The application server of claim 9, wherein the d-vine from the plurality of d-vines models a dependency between each pair of physiological parameters from the one or more physiological parameters, wherein a first set of physiological parameters from the one or more physiological parameters are continuous and a second set of physiological parameters from the one or more physiological parameters are discrete.

15. The application server of claim 9, wherein the rank transformation corresponds to an extended rank likelihood technique.

16. The application server of claim 9, wherein the health condition corresponds to at least one of a disease risk, a disease symptom, an onset of a disease, a recovery from a disease, or an effect of medications for a disease.

17. A computer program product for use with a health condition profiling system comprising one or more processors, a transceiver, and a display, the computer program product comprising a non-transitory computer readable medium, wherein the non-transitory computer readable medium stores a computer program code for assigning a health condition profile to a first human subject, wherein the computer program code is executable by one or more processors to:
extract a historical data comprising one or more records, wherein each of the one or more records includes a measure of the one or more physiological parameters associated with each of one or more second human subjects, wherein the historical data is missing values, comprises categorical data, or both;

cluster the historical data into a plurality of d-vines by sampling a plurality of latent variables based on a rank transformation of the historical data, wherein the transformed historical data does not include any missing values or categorical data;

estimate one or more latent variables from the plurality of latent variables based on:

a first count indicative of a number of the plurality of d-vines, a second count indicative of a number of the one or more records, a first value that is representative of a number of the one or more records clustered into a d-vine from the plurality of d-vines, and a second value that is representative of a parameter utilizable to predict a third value, wherein the third value corresponds to a probability of clustering the historical data into the d-vine from the plurality of d-vines;

generate the plurality of d-vines based on the estimated one or more latent variables from the plurality of latent variables;

train a classifier based on the generated plurality of d-vines, the classifier configured to sort data into one or more health condition categories, each health condition category corresponding to a health condition, wherein the historical data corresponds to a multivariate dataset from which the health condition is identifiable based on the generated plurality of d-vines;

sort a received measure of the one or more physiological parameters associated with the first human subject into one or more of the health condition categories using the trained classifier;

assign, by the one or more processors, a health condition profile to the first human subject, the profile comprising one or more health condition corresponding to the one or more categories into which the measure is sorted; and display the health condition on the display device;

wherein the transceiver is configured to receive the measure of one or more physiological parameters associated with a first human subject, wherein the one or more physiological parameters comprise at least one of an age, a cholesterol level, a heart rate, a blood pressure, a breath carbon-dioxide concentration, a breath oxygen concentration, a stroke score, a blood creatinine level, a blood albumin level, a blood sodium level, a total blood count, a blood glucose/sugar level, a blood hemoglobin level, and/or a blood platelet count.

* * * * *